US006300322B1

(12) United States Patent
Segall et al.

(10) Patent No.: US 6,300,322 B1
(45) Date of Patent: *Oct. 9, 2001

(54) PLASMA-LIKE SOLUTION

(75) Inventors: Paul E. Segall; Hal Sternberg; Harold D. Waitz; Judith M. Segall, all of Berkeley, CA (US)

(73) Assignee: BioTime, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/565,784

(22) Filed: May 5, 2000

Related U.S. Application Data

(63) Continuation-in-part of application No. 09/530,006, filed as application No. PCT/US97/19964 on Oct. 31, 1997, which is a continuation-in-part of application No. 08/886,921, filed on Jul. 2, 1997, now Pat. No. 5,945,272, which is a continuation of application No. 08/780,974, filed on Jan. 9, 1997, now abandoned, which is a continuation of application No. 08/364,699, filed on Dec. 28, 1994, now abandoned, which is a continuation-in-part of application No. 08/253,384, filed on Jun. 3, 1994, now Pat. No. 5,702,880, which is a continuation-in-part of application No. 08/133,527, filed on Oct. 7, 1993, now abandoned, which is a continuation-in-part of application No. 08/071,533, filed on Jun. 4, 1993, now Pat. No. 5,407,428.

(51) Int. Cl.$^7$ ............................ A01N 1/02; A61M 37/00; A61K 31/715
(52) U.S. Cl. .................................. 514/60; 604/4; 435/1.2
(58) Field of Search .................................. 435/1.2; 604/4; 514/60

(56) References Cited

U.S. PATENT DOCUMENTS

| Re. 34,077 | 9/1992 | Segall et al. . |
| 3,937,821 | 2/1976 | Irikura et al. . |
| 4,001,401 | 1/1977 | Bonsen et al. . |
| 4,061,736 | 12/1977 | Morris et al. . |
| 4,216,205 | 8/1980 | Radowitz . |
| 4,663,166 | 5/1987 | Veech . |
| 4,812,310 | 3/1989 | Sato et al. . |
| 4,908,350 | 3/1990 | Kramer et al. . |
| 4,923,442 | 5/1990 | Segall et al. . |
| 4,927,806 | 5/1990 | Kramer et al. . |
| 5,082,831 | 1/1992 | Leaf et al. . |
| 5,084,377 | 1/1992 | Rowan et al. . |
| 5,130,230 | 7/1992 | Segall et al. . |
| 5,171,526 | 12/1992 | Wong et al. . |
| 5,210,083 | 5/1993 | Pfirrmann . |
| 5,274,001 | 12/1993 | Borody . |
| 5,374,624 | 12/1994 | Segel . |
| 5,407,428 | 4/1995 | Segall et al. . |
| 5,702,880 | * 12/1997 | Segall et al. . |
| 5,945,272 | * 8/1999 | Seagall et al. . |

FOREIGN PATENT DOCUMENTS

| 437274A | 7/1991 | (EP) . |
| WO 89/10746 | 11/1989 | (WO) . |
| WO 92/18136 | 10/1992 | (WO) . |
| WO 94/28950 | 12/1994 | (WO) . |
| WO 96/19918 | 7/1996 | (WO) . |

OTHER PUBLICATIONS (1987)."6% Dextran 70 in 5% Dextrose injection or 0.9% Sodium Chloride injection" 06–3874–R8–Rev. Abbot Laboratories, North Chicago, IL 60064, USA.
(1992). "Media Formulas" ATCC Catalogue of Bacteria & Bacteriophages. p. 486.
Bailes et al. (1990). *Cryobiology*, vol. 27: 615–696(pp. 22–623).
Belzer et al., (1978). "Combination perfusion–cold storage for optimum cadaver kidney function and utilization" *Transplantation*, vol. 39(2): 118–121.
Bishop et al. (1985). "Evaluation of hypertonic citrate flushing solution for kidney preservation using the isolated perfused rat kidney" *Transplantation*, vol. 25(5): 235–239.
Collins (1977). "Hypothermic kidney storage" *Transplantation Proceedings*, vol. 9(3): 1529–1534.
Fischer et al. (1985). "Flush solution2, a new concept for one–to–three–day hypothermic renal storage preservation" *Transplantation*, vol. 39(2): 122–126.
Kallerhoff et al. (1985). "Effects of preservation conditions and temperature on tissue acidification in canine kidneys" *Transplantation*, vol. 39(5):485–489.
Leavitt et al. (1990). "Survival from prolonged cardiac arrest in totally exsanguinated hypothermic dogs" *FASB J.*. vol. 4(4): A963.
Lehninger (1975). *Biochemistry*, 2nd Edition, pp. 829ff.
Messmer "Characteristics, Effects, and Side Effects of Plasma Substitutes", Ch. 2 pp. 51–70.
Rosenberg, (1969). "Perspectives on the Problem of Blood Substitutes" *Proc. 12th Congr. Int. Soc. Blood Transf.* No. 3 Pt II pp. 737–745.
Ross et al. (1976). "72–hr canine kidney preservation without continuous perfusion" *Transplantation*, vol. 21(6): 498–501.
Segall et al. (1991). "Animal models in ice–cold bloodless medicine" *FASB J.*, vol. 5(4): A396.
Smith (1956). *Proc. Royal Soc.*, vol. 145: 395.
Spahn (1994). "Cardiovascular and coronary physiology of acute isovolemic hemodilution: a review of nonoxygen–carrying and oxygen–carrying solutions" *Anesth. Analg.*, vol. 78: 1000–1021.
Sternberg et al. (1990). "Interventive Gerontology, Cloning, and Cryonics" *Biomedical Advances in Aging*. Plenum Press, Ch. 19 pp. 207–219.
Wagner et al. (1993). "Pharacologic and clinical considerations in selecting crystalloid, colloidal, and oxygen–carrying resuscitation fluids, part 1" *Clin. Pharm.*, vol. 12: 335–347.
Waitz et al. (1991). "Hamsters live after hours of bloodless hyperbaric $O_2$" *FASB J.*, vol. 5(5): 4375.

* cited by examiner

Primary Examiner—William R. A. Jarvis
Assistant Examiner—Vickie Kim
(74) Attorney, Agent, or Firm—Bret E. Field; Bozicevic, Field & Francis

(57) ABSTRACT

Artificial plasma-like solutions and methods for their use are provided. The subject solutions include: electrolytes and an oncotic agent. The subject solutions find use in a variety of applications, particularly in those applications where at least a portion of a host's blood volume is replaced with a blood substitute.

21 Claims, No Drawings

PLASMA-LIKE SOLUTION

CROSS-REFERENCE TO RELATED APPLICATIONS

This application is a continuation-in-part of application Ser. No. 09/530,006 entitled Physiologically Acceptable Aqueous Solutions and Methods for their Use, which application was filed on Apr. 20, 2000 and is the United States National Phase application of International Application No. PCT/US97/19964 filed Oct. 31, 1997; which application is a continuation-in-part of U.S. application Ser. No. 08/886,921 filed Jul. 2, 1997 and now U.S. Pat. No. 5,945,272 which application is a continuation of U.S. application Ser. No. 08/780,974 filed Jan. 9, 1997 and now abandoned; which application is a continuation of U.S. application Ser. No. 08/364,699 filed Dec. 28, 1994 and now abandoned; which application is a continuation-in-part of U.S. application Ser. No. 08/253,384 filed Jun. 3, 1994 and now issued as U.S. Pat. No. 5,702,880; which application is a continuation-in-part of U.S. application Ser. No. 08/133,527 filed Oct. 7, 1993 and now abandoned; which application is a continuation-in-part of U.S. application Ser. No. 08/071,533 filed Jun. 4, 1993 and now issued as U.S. Pat. No. 5,407,428; the disclosures of which are herein incorporated by reference.

INTRODUCTION

1. Technical Field

The technical field of this invention is plasma-like solutions which may be used to substitute for the blood or plasma of a subject.

2. Background of the Invention

Physiologically acceptable solutions find use in a variety of different applications in the medical, biomedical research and related fields. For example, physiologically acceptable solutions find use as plasma substitutes in surgical applications which require the replacement of significant amounts of blood plasma volume. Such applications include treatments for blood lost during surgery or trauma, or when a tissue, organ, group of organs or an entire subject needs to be maintained at a hypothermic or frozen state. Such applications also include applications in which a patient's blood is flowed through an external device, such as a cardiopulmonary bypass machine, where the extra circulatory volume space resulting from attachment of the patient's circulatory system to the device must be filled with a compatible blood substitute, i.e. blood volume expander.

Physiologically acceptable solutions suitable for use as plasma expanders/substitutes must be able to mix freely with blood without unacceptably compromising its components, such as creating precipitates which significantly block flow in small vessels, destroying an unacceptable portion of its formed elements (cells, platelets), introducing agents or creating water, ionic or molecular imbalances destructive to body cells and tissues, or causing harmful physiologic activities such as inappropriate acceleration or inhibition of heartbeat, nerve conduction or muscle contraction, and the like.

The first plasma substitute solutions employed were derived from mammalian blood. Although such solutions have been used with success, because such solutions are derived from natural blood, they can contain various pathogenic substances, such as viral pathogens such as HIV, Hepatitis B, and other pathogens, e.g., prions such as those associated with Cruetzfeldt-Jakob disease, and the like. As such, use of blood substituted and plasma substitute solutions derived from natural blood are not free of complication.

As such, a variety of synthetic blood and plasma substitute solutions have been developed which are prepared from non-blood derived components. Although synthetic plasma-like solutions have found increasing use in a variety of applications, no single solution has proved suitable for use in all potential applications.

Accordingly, there is continued interest in the development of new physiologically acceptable aqueous solutions that are suitable for use as plasma substitutes. Of particular interest is the development of solutions that are suitable for use in hypothermic surgical applications, such as cardiac surgery and the like. Also of interest is the development of solutions that are terminally heat sterilizable.

Relevant Literature

Various physiologically acceptable solutions, particularly blood substitute solutions, and methods for their use are described in U.S. Pat. Nos.: RE 34,077; 3,937,821; 4,001, 401; 4,061,736; 4,216,205; 4,663,166; 4,812,310; 4,908, 350; 4,923,442; 4,927,806; 5,082,831; 5,084,377; 5,130, 230; 5,171,526; 5,210,083; 5,274,001; 5,374,624; 5,407,428 and 5,514,536.

Additional references describing physiologically acceptable solutions, including blood substitute solutions include: Bishop et al., Transplantation (1978) 25:235–239; Messmer et al., Characteristics, Effects and Side-Effects of Plasma Substitutes, pp 51–70; Rosenberg, Proc.12th Congr. Int. Soc. Blood Transf. (1969); Spahn, Anesth. Analg. (1994) 78:1000–1021; Biomedical Advances In Aging (1990) (Plenum Press) Chapter 19; Wagner et al., Clin. Pharm. (1993) 12:335; ATCC Catalogue of Bacteria & Bacteriophages (1992) p 486; and 06-3874-R8-Rev. May (1987) Abbott Laboratories, North Chicago, Ill. 60064, USA.

Additional references describing various applications of such solutions, including hypothermic applications, include: Bailes et al, Cryobiology (1990) 27:615–696(pp 622–623); Belzer et al., Transplantation (1985) 39:118–121; Collins, Transplantation Proceedings (1977) 9:1529; Fischer et al., Transplantation (1985) 39:122; Kallerhoffet al., Transplantation (1985) 39:485; Leavitt et al., FASEB J. (1990) 4: A963; Ross et al., Transplantation (1976) 21:498; Segall et al. FASEB J. (1991) 5:A396; Smith, Proc. Royal Soc. (1956) 145: 395; Waitz et al., FASEB J. (1991) 5.

Lehninger, Biochemistry ($2^{nd}$ Ed., 1975), pp 829ff provides a review of blood and its constituents.

SUMMARY OF THE INVENTION

Physiologically acceptable aqueous solutions and methods for their use are provided. The subject solutions include: electrolytes and an oncotic agent. The solutions find use in a variety of applications, particularly in applications in which at least of portion of a host's blood volume is replaced with a blood substitute solution.

DESCRIPTION OF THE SPECIFIC EMBODIMENTS

Physiologically acceptable aqueous solutions and methods for their use are provided. The subject solutions include: electrolytes and an oncotic agent. In certain embodiments, the solutions include at least one of calcium ion and a dynamic buffering system. The solutions may be used in a variety of applications and are particularly suited for use in applications where at least a portion of a host's blood is replaced with a substitute solution. In further describing the invention, the aqueous solutions themselves will be described first in greater detail followed by a discussion of various representative applications in which the solutions find use.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The aqueous solutions of the subject invention are physiologically acceptable, by which is meant that the solutions may be introduced into the vasculature of a host without inherently causing a toxic reaction. The solutions will have a pH ranging from about 4 to 10, usually from about 4.5 to 9 and more usually from about 5 to 8.5.

In one embodiment, the solutions will include a plurality of electrolytes, including: sodium ion, chloride ion, potassium ion and calcium ion. The sodium ion concentration of the solutions will range from about 70 to 160, usually from about 110 to 150, and in some embodiments from 130 to 150 mM. The concentration of chloride ion in the solution will range from about 70 to 170, usually from about 80 to 160, more usually from about 100 to 135 and in some embodiments from about 110 to 125 mM. The concentration of potassium ion will range from the physiological to subphysiological, where by "physiological" is meant from about 3.5 to 5, usually from about 4 to 5 mM, and by "subphysiological" is meant from about 0 to 3.5, usually from about 2 to 3 mM, where in many embodiments of the invention, the amount of potassium ion will range from about 1 to 5, usually from about 2 to 3 mM, where in certain embodiments, the amount of potassium ion may be higher than 5 mM and range as high as about 5.5 mM or higher, but will usually not exceed about 5.5 mM. The solutions will also include calcium ion in an amount ranging from about 0.5 to 6.0 mM, and in many embodiments will range from about 0.5 to 4.0, usually from about 2.0 to 2.5 mM, but in certain embodiments will range from about 4.0 to 6.0, usually from about 4.5 to 6.0 mM. The solutions may further include magnesium. When present, the magnesium ion will range from about 0 to 10 mM, usually from about 0.3 to 3.0 and more usually from about 0.3 to 0.45 mM.

In one embodiment, the solutions will include sodium ion and potassium ion, and optionally calcium ion. The sodium ion concentration of the solutions will range from about 70 to 160, usually from about 110 to 150, and in some embodiments from 130 to 150 mM. The concentration of potassium ion will range from the physiological to subphysiological, where by "physiological" is meant from about 3.5 to 5, usually from about 4 to 5 mM, and by "subphysiological" is meant from about 0 to 3.5, usually from about 2 to 3 mM, where in many embodiments of the invention, the amount of potassium ion will range from about 1 to 5, usually from about 2 to 3 mM, where in certain embodiments, the amount of potassium ion may be higher than 5 mM and range as high as about 5.5 mM or higher, but will usually not exceed about 5.5 mM. Optionally, the solutions may further include calcium ion. When present, the calcium ion will range from about 0.5 to 6.0 mM, and in many embodiments will range from about 0.5 to 4.0, usually from about 2.0 to 2.5 mM, but in certain embodiments will range from about 4.0 to 6.0, usually from about 4.5 to 6.0 mM.

The solutions may also include a dynamic buffering system, where the term dynamic buffering system is used to refer to one or more reagents that work in combination to keep the pH of the solution in a certain range in an in vivo environment. Preferably, the reagent members of the dynamic buffering system are normal biological components that maintain in vivo biological pH. The dynamic buffering system concept rests on the discovery by the inventors that compounds with no intrinsic buffering capacity in the biological range, such as lactate, acetate, or gluconate which are capable of being metabolized in vivo, act with other solution components to maintain a biologically appropriate pH in an animal, even at hypothermic temperatures and at essentially bloodless conditions. The dynamic buffering system of the present invention depends in part on oxygenation and removal of carbon dioxide ($CO_2$). The dynamic buffer of the invention has no or substantially no ability to act as a buffer outside of a biological system, i.e., a dynamic buffer maintains pH in the biological range in vivo but not in a cell free environment.

A critical component of the dynamic buffering system of the invention is a carboxylic acid, salt or ester thereof. By a carboxylic acid, salt or ester thereof is meant a compound having the general structural formula RCOOX, where R is an alkyl, alkenyl, or aryl, branched or straight chained, containing 1 to 30 carbons which carbons may be substituted, and preferably one of the carbon chains that compose the carbon chain of lactate, acetate, gluconate, citrate, pyruvate, or other biological metabolites; and X is hydrogen or sodium or other biologically compatible ion substituent which can associate at the oxygen position.

Optionally, the dynamic buffering system may further include a source of bicarbonate, usually sodium bicarbonate ($NaHCO_3$). When present, the concentration of $NaHCO_3$ will range from about 0.1 mM to 40 mM, usually from about 0.5 mM to 30 mM, and more usually from about 1 mM to 10 mM.

The solution of the present invention does not include a conventional biological buffer. By "conventional buffer" is meant a compound which in solution, in vitro, maintains pH at a particular range. By "conventional biological buffer" is meant a compound which in a cell-free system maintains pH in the biological range of 7–8. Examples of conventional biological buffers include N-2-Hydroxyethylpiperazine-N'-2-hydroxypropanesulfonic acid (HEPES), 3-(N-Morpholino) propanesulfonic acid (MOPS), 2-([2-Hydroxy-1,1-bis(hydroxymethyl)ethyl]amino)ethanesulfonic acid (TES), 3-[N-tris(Hydroxy-methyl)ethylamino]-2-hydroxyethyl]-1-piperazinepropanesulfonic acid (EPPS), Tris[hydroxymethyl]-aminomethane (THAM), and Tris [hydroxymethyl]methyl aminomethane (TRIS). Conventional biological buffers have a pK in the physiological range and function most efficiently in this range. Therefore, these buffers function independently of normal biological processes and are most potent in cell-free systems.

The absence of a conventional biological buffer in the solution of the invention confers several important medical advantages. For example, lower concentrations of buffers consisting of normal biological components are required to maintain in vivo pH, compared to conventional biological buffers. Conventional biological buffers may also pose toxicity problems. Further, the absence of a biological buffer allows the solution to be terminally heat sterilized. Generally, medical solutions are preferred to be terminally heat sterilized prior to use in a patient. The term "terminally heat sterilized" or "heat sterilized" as used herein refers to the process involving heating a solution to about 120° C. for 15 minutes under pressure, i.e., maintaining heat and pressure conditions for a period of time sufficient to kill all or substantially all bacteria and inactivate all or substantially all viruses in the solution. This procedure is normally performed in an autoclave, and is also known as "autoclaving". The purpose of heat sterilization is to kill possible infectious agents present in the solution. Infectious agents are known to tolerate temperatures up to 100° C. It is generally considered by the art that heating a solution under pressure to 120° C. for about 15 minutes is sufficient to insure sterility.

The solutions will also include an oncotic agent. The oncotic agent is included of molecules whose size is sufficient to prevent its loss from the circulation by readily traversing the fenestrations of the capillary bed into the interstitial spaces of the tissues of the body. As a group, oncotic agents are exemplified by blood plasma expanders. Compounds finding use as oncotic agents in the subject invention may be natural or synthetic, and will usually be polymeric compositions having an average molecular weight of at least about 40,000, usually at least about 100,000 and more usually at least about 200,000, where oncotic agents having a molecular weight of 300,000 or higher may find use. Examples of oncotic agents suitable for use in the solution of the present invention include proteinaceous compounds, such as albumin, e.g., human serum albumin, and cross-linked or high molecular weight hemoglobin, polysaccharides such as glucan polymers, and the like; organic polymers, e.g., PVP, PEG, etc.; and the like; where nonantigenic polysaccharides are preferred;

Polysaccharides that find use as oncotic agents in the subject solutions include hydroxyethyl starches, hydroxymethyl alpha (1 4) or (1 6) polymers, D-glucose polymers, e.g., dextrans having an alpha (1 6) linkage, cyclodextrins, hydroxypropylstarches, hydroxyacetylstarches, and the like.

Hydroxyethyl starches are of particular interest for certain embodiments of the subject invention. The average molecular weight of hydroxyethyl starches finding use in the subject invention may range from 10,000 to 1,000,000 d or higher, where the molecular weight will typically range from about 40,000 to 1,000,000, usually from about 100,000 to 900,000, and more usually from about 200,000 to 800,000 d. Preferred are compositions in which the average molecular weight of the hydroxyethyl starch oncotic agent ranges from about 50,000 to 1,000,000, usually from about 100,000 to 900,000 and more usually from about 200,000 to 800,000 d. The degree of substitution will range from about 4 to 10, where in certain embodiments, the degree of substitution will range from 7 to 10, in other embodiments will range from 4 to 5, and in other embodiments will range from 6 to 7. Therefore, one class of preferred solutions will include a hydroxyethyl starch with between about 6 and 7 hydroxyethyl groups for every 10 glucose units. Another class of preferred solutions will include between about 4 and 5 hydroxyethyl groups for every 10 glucose units. Yet another class of preferred solutions will include between about 7 and 8 hydroxyethyl groups for every 10 glucose units.

A particularly preferred oncotic agent is Hetastarch (McGaw, Inc.), an artificial colloid derived from a waxy starch composed almost entirely of amylopectin with hydroxyethyl ether groups introduced into the alpha (1 4) linked glucose units and having a molar substitution of about 0.7 hydroxyethyl groups/glucose unit. The average molecular weight of hydroxyethyl starch is 480,000 with a range of 400,000 to 550,000 and with 80% of the polymers falling in the range of 30,000 to 2,400,000 d. The colloid properties of a 6% solution (wt/wt) of Hetastarch approximates that of human serum albumin.

Another particularly preferred oncotic agent is Pentastarch, which has a molar substitution of about 0.45 hydroxyethyl groups/glucose unit and an average molecular weight range (as measured by the HPSEC method as reported in PDR 1996) of from about 150,000 to 350,000 d, with 80% between 10,000 and 2,000,000 d.

Another particularly preferred oncotic agent is "Hexastarch," which has a molar substitution of about 0.64 hydroxyethylgroups/glucose unit and an average molecular weight of about 220,000.

In certain embodiments, the hydroxyethyl starch will be a select fraction of the initial hydroxyethyl starch source, particularly a select size fraction, where generally the fraction will be at least one of the fraction having an average molecular weight of less than about 1,000,000 daltons or the fraction having an average molecular weight of greater than about 50,000 daltons. Conventional fractionation means may be used to prepare such fractions.

The concentration of oncotic agent in the solution is sufficient to achieve (when taken together with chloride salts of sodium, calcium and magnesium, organic ion from the organic salt of sodium and hexose sugar discussed above) colloid osmotic pressure approximating that of normal human serum, about 28 mm Hg. Generally, the amount of oncotic agent in the solution will range from about 0.5 to 30, usually from about 1 to 25 and more usually from about 2 to 8%. Where the oncotic agent is a hydroxyethyl starch, the amount present in the solution will range from about 1 to 30, usually from about 2 to 15 and more usually from about 4 to 8%.

The solution may further include one or more different optional agents which may be included in the solution to make the solution suited for a particular application. One optional agent that may be included, and usually is included, is sugar. The sugar will generally be a simple hexose sugar, such as glucose, fructose and galactose, of which glucose is preferred. In the preferred embodiment of the invention nutritive hexose sugars, are used and a mixture of sugars can be used. The sugar is typically, though not necessarily, present in the solution in a physiological amount. By the term "physiological amount" or "physiological levels" is meant the concentration of sugar is in a range between 2 mM and 50 mM with concentration of glucose of 5 mM being preferred. At times, it is desirable to increase the concentration of hexose sugar in order to lower fluid retention in the tissues of a subject. Thus the range of hexose sugar may be expanded up to about 50 mM or even above, but usually not above 60 and more usually not above 55 mM, if necessary to prevent or limit edema in the subject under treatment, except where the agent is present as a cryoprotective agent.

The solutions of the present invention may include a blood clotting factor able to accelerate or promote the formation of a blood clot. Preferred blood clotting factors for use in the solution of the invention include vitamin K, Factors I, II, V, VII, VIII, VIIIC, IX, X, XI, XII, XIII, protein C, von Willebrand factor, Fitzgerald factor, Fletcher factor, and a proteinase inhibitor. The concentration of the blood clotting factor is determined by one skilled in the art depending on the specific circumstances of treatment. For example, generally when vitamin K is administered, its concentration will be sufficient to deliver 5–10 mg to the patient.

The solutions of the present invention may include an oxygen-carrying component in a concentration sufficiently low so as not to be toxic to the subject. The oxygen carrying component will usually be present in a sufficient amount to deliver enhanced oxygen to the tissues of a subject without resulting in toxicity to the subject. A "sufficient amount" of an oxygen-carrying component is an amount allowing a resting subject with an unimpaired circulation and physiology to survive and recover from trauma, illness or injury. In normal humans at normal body temperature, this is at least 5–6 ml $O_2$/100 ml of intravascular fluid. Oxygen-carrying components include hemoglobin extracted from human and non-human sources, recombinant hemoglobin, hemocyanin, chlorocruorin and hemerythrin, and other naturally occurring respiratory pigments extracted from natural sources or made by recombinant DNA or in vitro methods. These compounds may be modified by a number of means known to the art, including by chemical crosslinking or covalent bonding to polyethylene glycol group(s). When the oxygen-carrying component is hemoglobin, it is preferably present in the concentration range of between about 20–200 g/l.

The solutions may further include one or more cryoprotective agents, where by cryoprotective agent is meant any agent that preserves the structural integrity of tissue under hypothermic, e.g., sub-zero, conditions, where in certain embodiments the cryoprotective agent will be an agent that disrupts, at least to a partial extent, the ordered crystal arrangement of water molecules in a manner such that the freezing point of the aqueous solution comprising the cryoprotective agent is lowered as compared to the freezing point of an analogous solution that does not include a cryoprotective agent. Cryoprotective agents of interest include: alcohols, particularly low molecular weight aliphatic alcohols, usually C1 to C6 alcohols, more usually C1 to C4 alcohols, such as methanol, ethanol, and the like; polyols, including linear, branched and cyclic polyols, usually low molecular weight aliphatic polyols, including diols, triols, and other polyols, such as sugars (described in greater detail below) where polyols of particular interest include diols, such as ethylenediol, propanediol, butanediol, triols, e.g., glycerol, and the like; sugars, including erythrose, threose, ribose, arabinose, xylose, lyxose, allose, atrose, glucose, mannose, gulose, idose, galactose, talose, erythrulose, ribulose, xylulose, psicose, fructose, sorbose, tagatose and disaccharides, e.g., sucrose, lactose and maltose, where glucose is particularly preferred; other agents such as timethylamine, trimethylamine oxide (TMAO), DMSO, urea, formamide, dimethylformamide and the like; clathrates, silicon comprising agents, such as silanes and the like, fluorocarbon compounds and derivatives thereof, etc.; where the cryoprotective agent may be forced into solution by pressure and/or a suitable surfactant agent may be employed, where such surfactant agents are known to those of skill in the art. Such agents will typically be present in amounts sufficient to provide the desired cryoprotective effect, where the particular amount of the agent will depend on the particular agent employed. When the agent is a polyol, e.g., a diol, it will generally be present in amounts ranging from about 0.2 to 1 M or 0 to 30%. With respect to propanediol, in particular a range of 0.2 M to 0.6 M is preferred and a concentration of about 0.4 M propanediol is most preferred. 1,2-propanediol is preferred as the adduct to the solution used for low temperature organ and donor preservation according to the invention, although 1,3-propanediol may be used. For TMAO, TMAO will be present in the solution in a final concentration in a range between 0.2 M and 7 M. When glycerol is employed, it will be present in a concentration ranging from about 0 to 40%, usually from about 5 to 30%, and more usually 5 to 20%. When DMSO is employed, it will be present in amounts ranging from about 0 to 40%, usually from about 5 to 30%, and more usually from about 5 to 20%. When a sugar is employed (particularly glucose), the sugar ranges between about 0.6 M to about 1.4 M, with 1.0 M being preferred for certain embodiments.

In preparing the subject solutions, the various constituents may be combined at substantially the same time, or added sequentially, as may be convenient. The solutions may be terminally heat sterilized as described above. As also described above, the solutions may further include agents that should not be terminally heat sterilized, such as a source of bicarbonate, where the bicarbonate participates in the dynamic buffering system. In such instances, the sodium bicarbonate will be added as a sterile solution to a pre-autoclaved "base solution." Similarly, when it is desirable to add a blood clotting factor or oxygen-carrying component, the blood clotting factor or oxygen-carrying component is added as a sterile solution to the autoclaved base solution.

For purposes of description of the invention, the mixture according to the invention has been discussed and will continue to be discussed in terms of an aqueous solution. From the following description of the invention, it is expected that one of ordinary skill in the art would be enabled to provide the mixture as a dry mixture and make the adjustments to amounts of sodium chloride and organic salt of sodium as necessary to accommodate the amounts of sodium chloride found in normal saline solution, which may be used as a diluent for the dry mixture according to the invention.

The subject solutions find use in a variety of different applications. The subject solutions find particular use in applications where it is desired to replace at least a portion of a host's (or tissue or organ thereof) circulating blood volume with a substitute solution, where such applications include: surgical procedures, including procedures involving a reduction in the temperature of a host from the host's normal body temperature; as a blood substitute; to maintain physiological integrity following death; as a cold preservation agent for tissue or organ; in regional chemoperfusion; and the like.

The solution may be used as a circulating solution in conjunction with oxygen or hyperbaric oxygen at normal body temperatures or during procedures when the subject's body temperature is reduced significantly below the subject's normal temperature. For example, during surgical procedures and in cadaver organ donation at low temperatures, the subject's blood may be replaced with the cold circulating solution of the invention, where the solution may be circulated for a time to perfuse and maintain the subject and its organs intact during the procedure.

The solution of the present invention may be administered intravenously or intra arterially to a euthermic subject which is placed in a pressurized atmosphere of increased oxygen concentration up to 100% oxygen or to such a subject undergoing a procedure during which the subject's body temperature is reduced significantly below the subject's normal temperature whether or not hyperbaric oxygen is used. While the solution is being, administered to and circulated through the subject, various agents such as cardioplegic agents may be administered either directly into the subject's circulatory system, administered directly to the subject's myocardium, or added to the circulating solution of the present invention. These components are added to achieve desired physiological effects such as maintaining regular cardiac contractile activity, stopping cardiac fibrillation or completely inhibiting contractile activity of the myocardium or heart muscle.

Cardioplegic agents are materials that cause myocardial contraction to cease and include anesthetics such as lidocaine, procaine and novocaine and monovalent cations such as potassium ion in concentrations sufficient to achieve myocardial contractile inhibition. Concentrations of potassium ion sufficient to achieve this effect are generally in excess of 15 mM, and magnesium may also be present in amounts in excess of about 0.5 mM.

During revival of a subject (after a period of subnormal temperature or cryogenic maintenance using the solution according to the invention to maintain the subject) the subject may be reinfused with a mixture of the solution according to the invention along with blood retained from the subject or obtained from blood donors. As the subject is warmed, whole blood is infused until the subject achieves an acceptable hematocrit, generally exceeding hematocrits of about 20%. When an acceptable hematocrit is achieved, perfusion is discontinued and the subject is revived after closure of surgical wounds using conventional procedures.

In general, the solution according to the invention is administered using an intravenous line (when the subject is at normal temperature) or to a chilled subject using a pumped circulating device such as a centrifugal pump, roller pump, peristaltic pump or other known and available circulatory pump. The circulating device is connected to the subject via cannulae inserted surgically into appropriate veins and arteries. When the solution is administered to a chilled subject, it is generally administered via an arterial cannula and removed from the subject via a venous cannula and discarded, stored or circulated.

The solution may be used in a variety of surgical settings and procedures. It may be useful in delicate neurosurgery where clear surgical fields are imperative and reduced central nervous system activity may be desirable and achieved by performing the procedure on a patient whose core temperature and/or cerebral temperature has been substantially reduced.

The solution may be used to maintain a subject (which has lost a significant amount of blood, e.g., 20% to 98% of its blood) at normal body temperatures in a pressurized environment at increased oxygen concentration above atmospheric oxygen tension up to 100% oxygen. The subject is maintained in a high oxygen concentration, either continuously or periodically, until enough blood components can be synthesized by the subject to support life at atmospheric pressure and oxygen concentration. The solution according to the invention may be used to maintain a subject at temperatures lower than normal body temperature and at a reduced rate of metabolism after traumatic life threatening injury until appropriate supportive or corrective surgical procedures can be performed. In addition the solution may be used to maintain a patient having a rare blood or tissue type until an appropriate matching donor can be found and replacement blood units or other organ can be obtained.

Surprisingly it has been discovered that it is possible to replace substantially all of a mammalian subject's circulating blood with the solution according to the invention and to maintain the subject alive without reinfusing blood into the subject. Substantially all of a mammalian subject's circulating blood is considered to be replaced when the subject's hematocrit drops below 10%. Hematocrit may be lower than 10% if $O_2$ is provided to the subject, or substantially lower than 10% in a hyperbaric $O_2$ chamber. The solution according to the invention can of course be used to maintain a subject having a hematocrit in excess of 10%.

The procedure for replacing substantially all of a mammalian subject's circulating blood may be carried out with the mammalian subject's body temperature being maintained at its substantially normal temperature. In addition the procedure may be carried out with cooling of the subject and reduction of the mammalian subject's body temperature below that of its normal temperature. Cooling may be accomplished by chilling the subject in an ice bath, ice-salt slurry, or cooling blanket. The subject may be further cooled by chilling the solution according to the invention prior to perfusing the subject with the solution.

In the procedure according to the invention for replacing substantially all of a mammalian subject's circulating blood, it is preferred that the subject is chilled and perfused with the solution, using an arterial catheter to deliver the solution to the subject's circulatory system and a venous catheter to remove blood and the perfusate from the subject. Substantially all of the subject's circulating blood is removed in this manner as determined by measurement of the hematocrit of the effluent from the venous catheter.

When substantially all of the subject's circulating blood is removed, perfusion may be stopped.

In addition, the procedure for replacing substantially all of the subject's blood may be carried out with the aid of hyperbaric $O_2$. The subject is placed in a hyperbaric chamber pressurized with oxygen at concentrations exceeding 20%, preferably 100% oxygen. The pressure of the hyperbaric chamber is maintained during most of the procedure in a range between 0.5 pounds per square inch over atmospheric pressure to pressures up to about twice atmospheric pressure. In one embodiment, the procedure is performed with the subject in a hyperbaric chamber at hyperbaric pressures of about 0.07 to about 2 atmospheres over ambient pressure (0.5–30 pounds per square inch [psi]) with 100% oxygen. If necessary, the pressure of the hyperbaric chamber may be reduced to atmospheric pressure during wound closure. The subject is subsequently maintained at hyperbaric pressure at high oxygen concentration. The pressure is gradually reduced to a lower pressure but one still hyperbaric. Preferably the pressure is maintained below 10 psi to about 5 psi for a number of hours to several days. Subsequently, the pressure is again gradually lowered below 1 psi and preferably to about 0.5 psi and is maintained at this pressure for an additional period of time up to a day or more.

The solution may also be used to maintain the physiological integrity of an organ donor subject immediately after the occurrence of brain death. The subject can be chilled, the subject's blood removed and replaced with a circulating solution maintained below 37° C., or while circulating cold solution according to the invention. Through this use of the solution, ischemia of vital organs can be minimized. By circulating cold solution according to the invention through the subject's circulatory system at low temperature with or without placing the subject in a hyperbaric oxygen chamber, vital organs can be maintained for longer periods of time, thus maximizing the number of organs that can be effectively used from one donor for potential transplant recipients.

In another aspect of the invention, it has been discovered that by using certain adducts, particularly propanediol and high concentration glucose to augment the solution, it may be possible to reduce the temperature of donor organs, and in particular donor hearts, below the freezing point of water (0° C.) and recover them from freezing in a useful state, i.e., a state capable of maintaining coordinated cardiac contraction. Furthermore by using the solution according to the invention with such adducts, it has been possible to reduce the temperature of intact mammalian subjects below the freezing point of water (0° C.) and restore them from freezing in a state capable of maintaining coordinated cardiac contraction and even respiration and conscious reaction. Other organ systems are also believed to be maintained with a high degree of biological integrity, i e., in a physiological state capable of maintaining life.

The following examples are offered by way of illustration and not by way of limitation.

EXPERIMENTAL

The following examples are put forth so as to provide those of ordinary skill in the art with a complete disclosure and description of how to carry out the synthesis of the invention and is not intended to limit the scope of what the inventors regard as their invention. Efforts have been made to ensure accuracy with respect to numbers used (e.g., amounts, temperature, etc.), but some experimental error and deviation should be accounted for. Unless indicated otherwise, parts are parts by weight, molecular weight is weight average molecular weight, temperature is in degrees Centigrade, and pressure is at or near atmospheric.

EXAMPLE 1

Solution Compositions

A. Composition of L solution. The composition of L solution is as follows: $Na^+$ 143 mM; $Ca^{++}$ 2.5 mM; $Mg^{++}$ 0.45 mM; $K^+$ mM 3.0; $Cl^-$ 124 mM; glucose 5 mM; and lactate 28 mM. The solution is filtered to remove undissolved material and placed in autoclavable containers and heated in an autoclave to a temperature of 120° C. for 15 minutes.

B. Composition of HL (DioTime Hextend™-lactate) Solution. L formulation with the addition of 60 g/l of high molecular weight Hetastarch.

C. Composition of HLB (BioTime Hextend™-lactate-bicarbonate) Solution. HL solution with the addition of 5 ml/l1 M solution of $NaHCO_3$.

D. Composition of HL-DL (BioTime Hetadex™-lactate) Solution. HL formulation except 6% Dextran 40 is used in place of 6% Hetastarch.

E. Composition of AL (BioTime Albextend™) Solution. L solution except with the addition of 50 g/l albumin. ALB solution is AL solution with the addition of 5 ml/l of a 1 M $NaHCO_3$.

F. Composition of HL-Heme Solution. HL solution with the addition of 20–200 g/l hemoglobin.

G. Composition of L-Heme Solution. L solution with the addition of 20–200 g/l hemoglobin.

EXAMPLE 2

Blood Replacement with HL-DL Solution

A 240 g female rat was anesthetized with ketamine, xylazine an acepromazine mixture injected i.m. The animal was placed on a stage and its right femoral artery and vein cannulated. The animal was perfused isovolemically with 10 ml of HL-DL solution until its hematocrit reached 17.2%. The cannulas were removed, vessels ligated, and the incision closed. The animal tolerated perfusion well, and was active and eating within 3 days of the procedure. The animal recovered fully and remained alive and healthy.

EXAMPLE 3

Reviving An Ice-Cold Blood-Substituted Dog

A 26.8 kg male dog was anesthetized with nembutal and intubated. It was moved to the operating room, ventilated, and catheterized with venous, Foley, arterial, and Swan-Ganz catheters, and after i.v. heparin, its right femoral artery and vein were cannulated. An esophageal tube was inserted and antacid administered. Temperature sensors were placed in the esophagus and the rectum. Methyl prednisolone was injected i.v.

The animal was wrapped in a cooling blanket, and surface cooling initiated. The animal's cannulas were connected to a bypass circuit, which consisted of a vortex blood pump, an oxygenator with a built-in heat exchanger, a secondary in-line heat exchanger, and a funnel for the rapid administration of blood and blood substitute. Whole blood (225 ml) was removed from the dog and saved for rewarming. Blood volume was quickly replaced with HLB solution. The bypass circuit containing 1.05 liters of HLB solution was opened to the animal, and core cooling began.

Thirty three liters of HLB solution were exchanged. After substantially all of the blood was removed, a sufficient amount of a blood 2 M KCl solution was infused to stop cardiac contraction. By the time the ice-point was approached, the hematocrit was far below 1%. The animal's deep esophageal temperature was below 10° C. for 4 hours and 5 minutes, with a minimum recorded temperature of 0.7° C.

Following the hypothermic period, the animal was warmed. When body temperature climbed past 10° C., venous effluent and whole blood previously collected, as well as donor blood, was returned to the circuit; hematocrit increased with increasing temperature. Lidocaine and bicarbonate were administered, the heart defibrillated, and ventilation begun. When blood pressure and body temperatures approached normal, the animal was weaned from bypass, and protamine and Lasix injected. Several hours after warm-up, the animal was conscious and responsive. The animal remained alive and healthy after the procedure.

EXAMPLE 4

Reviving an Ice-Cold Blood-Substituted Baboon

A 24 kg male baboon of the species Papio annubis was anesthetized first with ketamine and acepromazine i.m., then with i.v. pentothal. It was then immobilized with pancuronium bromide. It was intubated, ventilated, and catheterized with venous, Foley, and arterial catheters. The animal was wrapped in a cooling blanket, and surface cooling initiated. After i.v. heparin was administered, the baboon's right femoral artery and bilateral femoral veins were cannulated. Temperature sensors were placed in the esophagus, rectum and brain. The animal was instrumented for EKG, somatosensory evoked potentials (SSEPs) and EEG. Dexamethazone was injected i.v.

The animal's cannulas were connected to a bypass circuit, which consisted of a vortex blood pump, an oxygenator with a built-in heat exchanger, and a funnel for the rapid administration of blood and blood substitute. Whole blood (300 ml) was removed from the baboon and saved for rewarming.

The volume was quickly replaced with 300 ml of physiological saline solution. The bypass circuit, containing 2 liters of Plasmalyte (commercially available electrolyte solution), was opened to the animal and core cooling begun.

After the deep esophageal temperature declined below 13° C., another 2 liters of Plasmalyte containing 12.5 g of mannitol, was added to the circuit, replacing the mixture of blood and Plasmalyte which previously filled the circuit. This diluted blood was saved for use during warming. Immediately afterwards, 10 liters of HLB solution were added, replacing the Plasmalyte. By the time the ice-point was reached, the hematocrit was far below 1%. When the animal reached brain temperature of 3.4° C. and deep esophageal temperature of 2.8° C., the blood pump was stopped and the animal was maintained under a condition of circulatory arrest (standstill) for 45 minutes. After this period, circulation was resumed.

Following the hypothermic period, 4.2 liters of HLB solution were flushed through the animal while collecting venous effluent, and the animal warmed. When body, temperature reached 15° C., 2 liters of Plasmalyte were added to the circuit to replace the HLB solution. Mannitol (6.25 g/l) was added to the Plasmalyte in the circuit. Additionally, venous effluent and whole blood previously collected, as well as donor blood cells and fresh-frozen plasma, were returned to the circuit; the animal's hematocrit increased with increasing body temperature. Another 12.5 g of mannitol were added to the circuit. When the esophageal and rectal temperatures approached normal, the heart fibrillated during warming and began beating. Ventilation was begun. When blood pressure and body temperatures approached normal, the animal was injected with protamine i.v., weaned from bypass, its cannulas and catheters removed, and its incisions closed.

The animal's deep esophageal temperature had been below 15° C. for 3 hours, and below 10° C. for 2 hours 17 minutes, with a minimum recorded temperature of 2.8° C. (Table 3). The following morning, the animal was able to sit erect in its cage and pick up and eat pieces of banana, as well as drink apple juice. It remained alive and well until sacrificed more than one week later for histological evaluation.

EXAMPLE 5

Blood Replacement with Two Solution System in a Patient Undergoing Cardiopulmonary Bypass Surgery A patient is anesthetized, cannulated and instrumented for cardiopulmonary bypass. The patient is wrapped in a cooling blanket and surface cooled to 30° C. The patient is then placed on bypass with the circuit primed with ALB solution. The patient is core and surface cooled until his deep esophageal temperature reaches 20° C. Blood is collected with 4 L of ALB solution, and immediately replaced with HLB solution. The body is then cooled and maintained while surgical procedures are performed on the heart or brain. The patient is then warmed, and the HLB solution replaced first with ALB solution, and then with the ALB-blood solution originally removed. 5–10 mg of vitamin K is administered.

One of the advantage of using the ALB solution as a bypass prime and for blood collection is that when the patient's own hemodiluted blood is reinfused during warm-up, albumin functions as the naturally-occurring compound, maintaining blood oncotic agent without impeding the patient's own ability to synthesize albumin.

EXAMPLE 6

Emergency Blood-Substitution of Hemorrhaging Subject with HL-Heme Solution

A patient suffering from severe blood loss is infused with HL solution containing 5 mg/l of blood-clotting factor vitamin K and 30 g/l of the oxygen-carrying component hemoglobin. The patient's blood pressure is stabilized and normal oxygen delivery to the patient's tissues is resumed. The patient's body gradually clears the Hetastarch component while synthesizing its own albumin such that blood oncotic pressure remains stabilized during the recovery period.

Use of HL solution containing blood-clotting factors and oxygen-carrying components allows the use of substitute blood to be reduced or completely avoided.

EXAMPLE 7

Use of Blood Clotting Factor in Hemodiluted Mammals

Six young female rats (227–262 g) were anesthetized, their right femoral arteries and veins cannulated, and 40–60% of their blood replaced with HL solution. After hematocrits were reduced to 16–22%, the animals were slowly injected i.v. with 6 ml of Trasylol® (10,000 KIU/ml). Their tails were severed 30 mm above the tip. Blood loss averaged 0.39±0.06 (mean±SEM) ml, and all but one animal survived at least one day. Eight control animals were similarly perfused with HL solution, but were not given Trasylol® injections. The average blood loss was 4.8±0.54 ml, and only 3 of the 8 animals survived. Compared to untreated controls, mortality (P<0.02) and blood loss (P<0.002) in the HL-treated animals without Trasylol® was significantly greater.

EXAMPLE 8

Ice-Cold Blood Substitution of a Dog with Solution HLB.

Place a 25–30 Kg dog on partial cardio-pulmonary bypass. Surface and core cool the dog to near the ice point (1–3° C.). Replace the dog's blood with solution HLB hypothermic blood substitute, described in Example 1. Retain the blood for transfusion during rewarming. Reduce the animal's body temperature to near the ice point (below 4° C.) and then rewarm. Replace the blood substitute with blood with warming and revive the animal.

Preparation. Catheterize the dog by means of the right radial vein, injected iv with pentothal, then fit with an endotracheal tube and ventilate with isofluorane (or Flether) in 100% $O_2$. Initiate a Ringer's lactate drip at a rate titrated to the dog's arterial blood pressure (approx. 40 ml/hr.iv). Place the dog on a cooling blanket cooled with recirculating ice water. Catheterize the right carotid artery to allow for blood pressure CAP) monitoring, and add a 3-way stopcock in-line to allow arterial blood sampling every 10–60 min. throughout the entire procedure. Insert a foley catheter for urine collection and measure the urine volume throughout the procedure. Implant a 2 lumen, 7 F, Swan Ganz wedge catheter via the right jugular vein or right femoral vein, which is fed through the right heart into the pulmonary artery. Use the distal port to measure pulmonary wedge pressure (PAW), the proximal port is used for central venous pressure (CVP). (1f necessary CVP may be measured with a catheter inserted in one of the brachial veins.) Isolate the left femoral artery and vein and prepare for cannulation. Heparinize the animal (approx. 5,000 u). Insert a Biomedicus venous return cannula (15–19 F) in the femoral vein and a Biomedicus arterial cannula (12–15 F) in the femoral artery. Measure the activated clotting time (ACT) every 45 min. (until blood substitution) and adjust the heparin such that it remains greater than 400 sec. Attach a thermocouple approx. midway to an esophageal tube and insert the unit so that the tube enters the stomach. A second thermocouple is placed rectally. Attach ECG leads. Add Solu-Delta-Cortef (Upjohn, veterinary prednisolone Na succinate), 80 mg by iv injection. Coat the eyes with Terrimycin (or Lacrylube), and add DiGel (or Maalox, 20 ml) through the esophageal tube.

Measurements. Measure arterial blood gasses, pH and hematocrit in every blood sample, and in some cases electrolytes, enzymes and other chemistries. Monitor esophageal and rectal temperature as well as the arterial inflow and venous return blood temperatures. Monitor CAP, PAW, CVP, ECG, and airway pressure. Temperatures should be displayed digitally and stored as a function of time in a computerized data acquisition system. The pressures and ECG should be displayed as real time waveforms or as numerical data and stored by the computer.

Bypass Circuit Components. The circuit features a Biomedicus centrifugal blood pump and flow meter, a Terumo hollow fiber membrane oxygenator with built-in heat exchanger, Shiley hard shell venous reservoir with filter and a secondary heat exchanger with integral bubble trap (Electromedics) located as close to the animal as possible. A drain segment is located near the inlet of the venous reservoir and terminates with a check valve. This allows rapid and efficient blood/blood-substitute exchanges. There is an A-V shunt segment that allows circulation when not on bypass.

The venous reservoir can be filled from either the 1 liter separatory funnel through the "quick prime" port or from dual infusion bags through one of the cardiotomy ports. The arterial line from the oxygenator to the arterial cannula and the A-V shunt are constructed from ¼" tubing; the venous return, drain and pump-head lines are ⅜". In those segments where severe bending can occur, heavy-wall tubing is used or the tube is braced with "spiral wrap."

The patient loop is double wrapped and the entire circuit (sans the factory sterilized reservoir, secondary heat exchanger and oxygenator) is ethylene oxide gas sterilized as six basic sections (pump-head, flow meter section, central bypass loop, funnel, infusion line, and gas filter line).

Bypass Circuit Support. Ice water, pumped from one of two 10 gal. insulated reservoirs, is used to cool the oxygenator and secondary heat exchangers. The other reservoir supplies the cooling blanket. At the onset of surgery, ice water is circulated through the cooling blanket. At the onset of bypass, room temp. water is circulated through the circuit heat exchangers.

Temperature is slowly decreased by adding ice to the reservoir, in quantities sufficient to maintain a 7–10° C. difference between the esophageal and blood stream temperatures. After blood substitution (i.e., to a hematocrit of less than about 4%) full ice water flow is commenced.

Upon rewarming, ice is removed from the reservoir and the heater is activated. The temperature of the warming stream is limited to a maximum of 10° C. greater than the venous return temperature, by manual adjustment of the heater thermostat.

The oxygenator is supplied with sterile, filtered 100% $O_2$.

Blood Substitution. The circuit is primed with 2 liters of solution L (Example 1), and recirculated through the A-V shunt to ensure temperature-gas equilibrium. The cannulas are attached to the arterial and venous lines of the bypass circuit, and the lines remain clamped. The cooling blanket is wrapped around the patient who is surface cooled until a deep esophageal temperature of 35° C. is reached.

The clamps are removed, and bypass is commenced with the solution L-diluted blood stream at room temperature (approx. 25° C.). At the onset of cooling, gaseous anesthesia is discontinued, and the dog is managed with 2.5% pentothal.

The blood stream is gradually cooled until the animal has an esophageal temperature of 20° C., at which time blood is removed by clamping the venous return at the reservoir inlet and draining from the drain segment while L solution is infused. During this exchange, an additional 2 liters of L solution is added to the venous reservoir and when the level of L solution drops to 250 ml, approximately 6 liters of HLB is added stepwise until all of the blood is removed (HCT less than 2%, visual observation). Approximately 4 liters of blood/blood-substitute mixtures collected in sterile bottles and retained for reinfusion. The very dilute blood mixture (about 5½ liters) is discarded.

After 4 liters have been exchanged (i.e., after the addition of 2 liters of solution L and 2 liters of solution HLB), 20 meq KCl will be injected via a stopcock on the secondary heat exchanger, to arrest the heart. During the exchange, the inflow is adjusted such that the PAW is kept below 5 mm Hg and the rate of efflux equals the rate of influx, i.e., as close to isovolemia as possible. At the end of the exchange the final reservoir level will be about 500 ml, the PAW below 5 mm Hg and the CVP less than 5 mm Hg. Flow will be adjusted such that isovolemia will be maintained (constant reservoir level and the above pressure levels, i.e., PAW<5 mm Hg and CVP<5 mm Hg).

When almost all of the blood is removed (HCT less than 4%, visual observation), the cooling stream can be reduced to ice water temperature (filling the reservoir with ice), and the dog rapidly cooled to its minimum temperature. If the HCT is observed to rise at any time during cold perfusion, the blood mixture can be removed by exchanging with 2 to 4 liters of solution HLB by the method described above.

During the entire procedure, arterial blood samples are taken and blood gasses, pH, HCT, and in some cases electrolytes, and other blood chemistries monitored.

After about 1–2 hours of blood substituted cooling, the dog's temperature will be about 1–4° C., and rewarming will begin. The dog will be rewarmed, by removing the ice from the supply reservoir and warming its contents with the heater which in turn warms the blankets. When the esophageal temp reaches 15° C., 4 liters of solution L with 25 g mannitol will be exchanged with the solution HLB followed by the 4 liters of collected blood mixture. The effluent will be discarded.

The animal will be transfused with stored autologous or donor blood and warmed gently with a warming temperature differential less than 10° C. and never above 40° C. The heart will spontaneously begin to beat or will be defibrillated. When the animal's temperatures (esophageal and rectal) reach about 35° C., physiological parameters are stabilized, and it can support itself, it can be weaned from the extracorporeal circuit.

EXAMPLE 9

Concentrated Aqueous Solution of Magnesium and Potassium for Cardioprotection

The discovery disclosed here is a novel product, specifically, an aqueous solution consisting of high concentrations of $K^+$ and $Mg^{2+}$ to be used in conjunction with ice cold HLB blood substitution in subjects requiring low-temperature surgery, in subjects requiring cardioplegia, or in organ donors to better preserve organs—such as hearts—prior to transplantation.

This solution can be used in conjunction with hypothermic total body washout with the HLB solution at cold temperatures to provide better cardiac protection during periods of circulatory arrest. The solution can also be used as a cardioplegia agent along with HLB in standard cardiac surgery procedures not involving total body washout, or to preserve the heart for transplantation after total body washout with cold HLB solution.

In preparing the high concentration solution of Mg and K, $MgSO_4$ and KCl have been used. These compounds are currently available in a form approved for use in human patients by the US FDA. However, $MgCl_2$ may substitute for $MgSO_4$ and KOH may also be useful in providing a basic pH at about 7.8 (range 7.2–8.4). Other substances which may be used in preparation of the high concentration solution of K and Mg are $KHCO_3$, $K_2PO_4$, K lactobionate, K citrate, K acetate and K gluconate, as well as the addition of $NaHCO_3$ to the solution containing $K^+$ and $Mg^{++}$. The end result however being a solution containing approximately 1.5 M potassium and 0.5 M magnesium.

Initially, a solution containing 50 mM KCl and 10 mM $MgSO_4$ in HLB solution was prepared. Approximately 1 to 2 ml of this solution was administered iv or intra-arterially to induce cardiac arrest of a small ice-cold blood substituted hamster. This volume corresponds to about 30–50% of a blood hamster's blood volume. It was discovered experimentally that this solution, when bolused intravascularly just upon completion of total body washout, induces cardiac arrest.

It was found that when about 9.5 ml of a 50% solution of $MgSO_4 \cdot 7H_2O$ (i.e., approx. 2M) and 27 ml 2M KCl was administered intra-arterially into ice cold dogs (body weights about 25 kg, with estimated blood volumes of about 1.8 liters) whose blood was replaced with HLB, significantly better protection of the heart resulted compared to that when no additional K and Mg is administered or when a more diluted K/Mg solution is administered (i.e., first dissolving the concentrated K/Mg solution in approximately 500 ml HLB solution in an oxygenator reservoir, and further diluting the solution in a circuit containing an additional 850 ml of HLB, which would create a 6.2 mM $Mg^{++}$ and 17.4 mM $K^+$ solution).

The solution, containing about 37 ml of 0.55M $MgSO_4 \cdot 7H_2O$ and 1.48M KCl, was adminstered into a component of the bypass circuit (heat exchanger) which was directly connected to the femoral artery of the subject. Based on this dog experimentation, this solution is expected to provide improved cardiac protection in subjects whose blood is replaced with HLB at low temperature.

Similarly, when delivering 0.1 ml of a high concentration $Mg^{++}/K^+$ mix intra-arterially into hamsters, it effectively provides cardiac protection when used just after hypothermic total body washout with HLB.

The novel discovery described here is the use of a solution consisting of extremely high concentrations of Mg and K which can be administered safely and effectively to induce cardioprotection particularly in conjunction with cold subjects whose blood has been replaced with HLB. The concentration of $K^+$ and $Mg^{++}$ administered is more than 10 times higher (for both electrolytes) than previously used or described to protect cold hearts.

1. Revival of a hamster using HLB and concentrated Mg/K solution.

A 55 g female hamster, fasted overnight was anesthetized with Ketamine 0.03 ml (100 mg/ml solution) and covered with crushed ice to lower rectal temperature to about 13° C. The animal was then placed on a surgical platform under a stereo microscope. Cannulas were placed in the carotid artery and jugular vein. The HLB solution was perfused into the artery while venous effluent was collected. The blood was replaced with ice-cold HLB solution. When about 65% of the blood was removed, the animal's temperature was lowered to about 1° C. Ventilation with 100% $O_2$ was initiated when the animal's temperature fell below 10° C. Approximately 7 ml or 2 blood volumes was required to replace most of the circulating blood. Upon cessation of perfusion, a 0.2 ml bolus (I.V.) of 0.5M KCl with 0.1M $MgSO_4$ was given. The heart arrested immediately. The animal was maintained in cardiac arrest for 5 hrs and 30 min. The animal was then perfused with 3 ml HLB followed by blood taken from donor animals. Upon gradual rewarming, normal heart beat and breathing resumed. On recovery, the animal demonstrated an ability to respond to stimuli, such as gentle pressure on the abdomen or paws.

2. A 70 g hamster, fasted overnight, was anesthetized with 0.03 ml ketamine (100 mg/ml solution) and covered with crushed ice to lower rectal temperature to about 13° C. The animal was then placed on a surgical platform under a stereo microscope. Cannulas were placed in the carotid artery and jugular vein. The HLB (with added glucose 50 mM and 5 mM $NaHCO_3$) solution is perfused into the artery while venous effluent is collected. The blood was replaced with ice-cold HLB solution. When about 65% of the blood was removed the animals temperature was lowered to about 1° C. Ventilation with 100% O2 was initiated when the animals temperature fell below 10° C. Approximately, 7 ml or 2 blood volumes is required to replace most available blood.

A solution consisting of 0.02 ml 1M $MgSO_4$ plus 0.1 ml KCl 1M is diluted with 0.1 ml HLB. Then the final 0.22 ml solution is administered iv. This corresponds to delivery of a cocktail 0.5M KCl and 0.09M $MgSO_4$. After 5 hours of circulatory arrest the animal is perfused with 3 ml HLB then blood taken from donor hamsters. As the animal is warmed, heart beat, breathing, and responsivity resume.

Previous to the discovery of using the Mg/K concentrate it was not possible to repeatedly obtain such results with regard to revival of hamster after 5 hours of cardiac arrest.

3. A 70 g female hamster, fasted overnight, was anesthetized with Ketamine 0.03 ml (100 mg/ml solution) and covered with crushed ice to lower rectal temperature to about 13° C. The animal was then placed on a surgical platform under a stereo microscope. Cannulas were placed in the femoral artery and jugular vein. The HLB solution is perfused into the artery while venous effluent is collected. The blood was replaced with ice-cold HLB solution. When about 65% of the blood was removed the animals temperature was lowered to about 1° C. Ventilation with 100% O2 was initiated when the animals temperature fell below 10° C. Approximately, 5 ml was infused. Then 0.2 ml of a cocktail 0.5M KCl and 0.09M $MgSO_4$ is administered intra-arterially. Then 1 ml of HLB was injected to chase the "cardioprotectant" up the circulatory system and into the tissues. The animal was maintained in circulatory arrest for 1 hour. Then the animal was perfused with 4 ml HLB and blood from donors while being rewarmed gradually. It was observed the hamster's heart resumed a normal EKG signal, followed by spontaneous breathing, responsiveness, consciousness, upright posture and long term survival.

Previously, long term survival was only rarely accomplished in such experiments without use of the K/Mg concentrate.

EXAMPLE 10

Method for Using HLB Involving Intermittent Perfusion with Additional Bicarbonate During periods of ice-cold blood substitution and circulatory arrest it was found that certain neurologic recovery takes longer compared to continuous circulation of HLB solution. In experiments on hamsters improved results were obtained using both extra bicarbonate in HLB and/or intermittent perfusion with HLB to reduce acidosis. This also prevents rigor and improves recovery especially of brain function as noted by responsivity following long periods of cardiac arrest in hamsters.

It has also been found that slow continuous perfusion of cold HLB blood substituted dogs appears to provide longer periods of cardiac arrest time than without continuous perfusion.

In hamsters it was found that additional bicarbonate, 5 mM, can be helpful at reducing acidosis after long periods of circulatory arrest.

1. A 60 g hamster, fasted, was anesthetized with Ketamine 0.03 ml (100 mg/ml solution) and covered with crushed ice to lower rectal temperature to about 13° C. The animal was then placed on a surgical platform under a stereo microscope. Cannulas were placed in the carotid artery and jugular vein. HLB solution (with added glucose 50 mM and 5 mM $NaHCO_3$) was perfused into the artery while venous effluent was collected. When about 65% of the blood was removed the animals temperature was lowered to about 1° C. Ventilation with 100% $O_2$ was initiated when the animals temperature fell below 10° C. Approximately, 7 ml or about 2 blood volumes is required to replace most available blood. The additional 5 mM $NaHCO_3$ provided a final pH of 8.5. After perfusion, the heart was stopped with 0.5 ml of 50 mMKCl and 10 mM $MgSO_4$. After 4 hours and 40 minutes the animal was re-perfused with 2 ml HLB followed by perfusion of blood taken from donor animals. The animal did not recover to breathing and responsiveness.

2. The same experiment was performed as in 1 above except that an intermittent perfusion of bicarbonate was introduced for 15 minutes 2 hours and 30 minutes after circulatory arrest.

A 60 g hamster, fasted, was anesthetized with Ketamine 0.03 ml (100 mg/ml solution) and covered with crushed ice to lower rectal temperature to about 13° C. The animal was then placed on a surgical platform under a stereo microscope. Cannulas were placed in the carotid artery and jugular vein. The HLB (with added glucose 50 mM and 5 mM $NaHCO_3$) solution was perfused into the artery while venous effluent was collected. The blood was replaced with ice-cold HLB solution. When about 65% of the blood was removed the animals temperature was lowered to about 1° C. Ventilation with 100% $O_2$ was initiated when the animals temperature fell below 10° C. Approximately 7 ml or 2 blood volumes was required to replace most available blood. Perfused HLB (containing an additional 50 mM glucose) plus an additional 5 mM $NaHCO_3$ which provided a final pH of 8.5. After perfusion, the heart was stopped with 0.5 ml of 50 mM KCl and 10 mM $MgSO_4$. After 2 hours and 30 minutes, the animal was perfused with HLB for 15 minutes (i.e., 2 ml HLB). After 4 hours and 40 min re-perfused with 2 ml HLB followed by blood from donor animals and warmed. The animal revived to breathing and responsivity. The time of cardiac arrest was over 5 hours.

EXAMPLE 11

Cryoprotective Solutions

1. Preparation of Solution
   a. Method 1
   To prepare 50 ml of a 10% glycerol solution in HLB, 0.45 ml of HLB is poured into a tube. Then 5 ml of 100% glycerol is added. The solution is shaken and filtered through 0.2 micron filter or less.
   b. Method 2
   For 1 liter HLB 15% glycerol: Add HES 60 g/l; NaCl 6.72*g/l bring volume to ½ final volume i.e., 500 ml with de-ionized water. Add and dissolve by shaking one chemical at a time $MgCl_2$ 0.09 g/l; $CaCl_2$ 0.37 g/l; KCl 0.22 g/l; glucose 0.9 g/l; Na Lactate (60% syrup) 4.03 ml/L; $NaHCO_3$ 0.42 g/l or 0.84 g/l (the additional bicarbonate may help reduce acidity). Bring to 850 ml with de-ionized water. Add 150 ml 100% glycerol. Filter 0.2 u
   * the amount of NaCl added is adjusted upon accounting for NaCl in starch note: with 50 mM extra glucose add 9 g/l additional glucose with shaking 1. A Cryoprotective Solution of 10% Glycerol in HLB Allows Revival of Partially Frozen Hamsters.

A 60 g female hamster, fasted overnight was anesthetized with Ketamine 0.03 ml (100 mg/ml solution) and covered with crushed ice to lower rectal temperature to about 13° C. The animal was then placed on a surgical platform under a stereo microscope. Cannulas were placed in the carotid artery and jugular vein. The blood was replaced with 2 ml ice-cold HLB solution followed by cryoprotective solution of HLB plus 10% glycerol. When about 65% of the blood was removed the animals temperature was lowered to about 1° C. Ventilation with 100% $O_2$ was initiated when the animals temperature fell below 10° C. After perfusion of 5 ml of cryoprotective solution, the heart was arrested with 50 mMKCl and 10 mM $MgSO_4$ (1.5 ml i.v.). Animals were then placed in a plastic bag and immersed in a cooling bath set at −15° C. After 30 minutes rectal temperatures dropped as cold as −2.2° C.

The animal was thawed, reperfused with HLB and then with donor blood. Upon rewarming, normal EKG signals are observed followed by breathing and responsiveness. Massive and extensive lesions (micro-hemorrhages) were observed in the brain upon necropsy demonstrating that the brain was substantially frozen under these conditions. However, despite freezing animals can recover to responsiveness.

2. Cryoprotective solution of 10% glycerol and 10% DMSO

A 60 g female hamster, fasted overnight was anesthetized with Ketamine 0.03 ml (100 mg/ml solution) and covered with crushed ice to lower rectal temperature to about 13° C. The animal was then placed on a surgical platform under a stereo microscope. Cannulas were placed in the carotid artery and jugular vein. The blood was replaced with 1.5 ml ice-cold HLB solution followed by cryoprotective solution of HLB plus 10% glycerol and 10%DMSO. When about 65% of the blood was removed the animals temperature was lowered to about 1° C. Ventilation with 100% $O_2$ was initiated when the animals temperature fell below 10° C. After about 6.5–7.0 ml of cryoprotective solution was perfused and the heart was arrested with 50 mMKCl and 10 mM $MgSO_4$ (1.5 ml i.v.) The animals were placed in a plastic bag and immersed in a cooling bath set at −15° C. After 30 minutes rectal temperatures dropped as cold as −1.5° C.

Upon thawing and reperfusion with HLB followed by donor blood, normal heart beat, breathing and responsiveness resumed. Massive and extensive lesions were observed in the brain upon necropsy demonstrating that the brain was substantially frozen under these conditions and that despite freezing animals can recover to responsiveness.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An aqueous solution comprising:

hydroxyethyl starch having an average molecular weight of 150,000 daltons or higher;

$Na^+$ in a range from about 70 to 160 mM;

$Cl^-$ in a range from about 70 to 160 mM;

$K^+$ in a range from about 0 to 5 mM; and $Ca^{2+}$ in an amount of at least 0.5 mM.

2. The solution according to claim 1, wherein said hydroxyethyl starch has an average molecular weight ranging from 400,000 to 550,000 daltons.

3. The solution according to claim 1, wherein said hydroxyethyl starch is Hetastarch.

4. The solution according to claim 1, wherein said hydroxyethyl starch has an average molecular weight ranging from 150,000 to 350,000 daltons.

5. The solution according to claim 1, wherein said hydroxyethyl starch is Pentastarch.

6. The solution according to claim 1, wherein said solution further comprises $K^+$ in a range from about 2 to 3 mM.

7. The solution according to claim 1, wherein said solution further comprises $Mg^{2+}$ in a range from about 0 to 10 mM.

8. The solution according to claim 1, wherein said solution further comprises a dynamic buffering system.

9. The solution according to claim 8, wherein said dynamic buffering system comprises an organic carboxylic acid, salt or ester thereof.

10. The solution according to claim 1, wherein said solution does not include a conventional biological buffer.

11. The solution according to claim 1, wherein said solution further comprises a simple sugar.

12. An aqueous solution comprising:

hydroxyethyl starch;

$Na^+$ in an amount of at least 110 mM;

$K^+$ in a range from about 0 to 5 mM; and at least one of $Ca^{2+}$ in an amount of at least 0.5 mM and a dynamic buffering system, wherein when said dynamic buffering system comprises lactate, said lactate is present in an amount of at least about 5 mM.

13. The solution according to claim 12, wherein said hydroxyethyl starch has an average molecular weight ranging from 400,000 to 550,000 daltons.

14. The solution according to claim 12, wherein said hydroxyethyl starch is Hetastarch.

15. The solution according to claim 12, wherein said hydroxyethyl starch has an average molecular weight ranging from 150,000 to 350,000 daltons.

16. The solution according to claim 12, wherein said hydroxyethyl starch is Pentastarch.

17. The solution according to claim 12, wherein said dynamic buffering system comprises an organic carboxylic acid, salt or ester thereof.

18. The solution according to claim 12, wherein said solution does not include a conventional biological buffer.

19. The solution according to claim 12, wherein said solution further comprises a simple sugar.

20. In a method where an aqueous composition is introduced into the circulatory system of a host or portion thereof, the improvement comprising:

introducing a solution according to claim 1.

21. In a method where an aqueous composition is introduced into the circulatory system of a host or portion thereof, the improvement comprising:

introducing a solution according to claim 12.

* * * * *